United States Patent [19]

Käymkö et al.

[11] Patent Number: 4,902,626
[45] Date of Patent: Feb. 20, 1990

[54] PROCEDURE AND APPARATUS FOR ASSURING POSITIVE IDENTIFICATION OF SAMPLES FOR ANALYSIS

[75] Inventors: Kimmo J. Käymkö; Pekka V. J. Röönea; Raimo K. Vaintola, all of Espoo, Finland

[73] Assignee: Kone Oy, Helsinki, Finland

[21] Appl. No.: 56,275

[22] Filed: May 26, 1987

Related U.S. Application Data

[63] Continuation of Ser. No. 654,638, Sep. 25, 1984, abandoned.

[51] Int. Cl.⁴ ............................................. G01N 35/04
[52] U.S. Cl. ..................................... 436/48; 116/202; 422/64
[58] Field of Search ................. 422/63, 64, 65, 67, 422/104, 119; 436/45, 47, 48, 55; 116/202; 73/863.01, 864.91

[56] References Cited

U.S. PATENT DOCUMENTS 1,763,476  6/1930  Morris ................................. 116/202
3,942,952  3/1976  Atwood ................................. 422/64
4,043,756  8/1977  Sommervold ......................... 436/47
4,276,258  6/1981  Ginsberg et al. ..................... 422/64
4,549,170 10/1985  Serres et al. ........................ 340/568

Primary Examiner—Michael S. Marcus
Attorney, Agent, or Firm—Martin Smolowitz

[57] ABSTRACT

A procedure for assuring the identification of samples when transferring such samples into a sample register for the measuring process by an apparatus performing analysis of the samples. The apparatus consists of a sample register, through apertures in its cover a sample container is insertable into the sample register at one desired location only. The computer of the apparatus performing the analysis finds the address of a given sample in its memory and moves the sample register relative to the cover so as to make the respective location in the register accessible through the aperture. When this takes place in the order in which the samples were presented, all confusion of samples will be avoided because the computer retains the address of each patient sample in its memory throughout the analysis procedure.

9 Claims, 1 Drawing Sheet

PROCEDURE AND APPARATUS FOR ASSURING POSITIVE IDENTIFICATION OF SAMPLES FOR ANALYSIS

This application is a continuation of application Ser. No. 654,638, filed 9/25/84, now abandoned.

BACKGROUND OF THE INVENTION

The present invention concerns a procedure for assuring the identification of samples for analysis when the samples are transferred into a sample register for a measuring process in an apparatus for performing analysis of the samples.

A general principle when samples are analyzed is that the samples to be analyzed in succession are placed in a sample cup-holder or equivalent sample disk, where the cups or containers can be disposed in any position in an analyzer apparatus. This sample placement is accomplished manually, and the handling of samples requires great precision and systematic work from the person making the analysis, for the sample cup not to be placed in a wrong position on the sample disk or register of the analyzer apparatus.

Since confusion among the samples may be caused by the human factor, particularly when extensive sample series are examined, the need has been recognized to develop a procedure and means which eliminates these risks. The risk of confusion increases with the number of samples handled and with the operator's lack of training, resulting in possible serious errors.

SUMMARY OF THE INVENTION

The object of the present invention is to provide a procedure for assuring positive identification of samples for analysis, which eliminates the risk of laboratory samples being inaccurately placed and mixed when they are processed in a laboratory analyzer.

In order to achieve the desirable effect mentioned, the procedure of the invention is mainly characterized in that the desired sample register opening location in the analyzer and an aperture in the cover of the sample register are placed in alignment, whereafter the sample container is inserted manually in the sample register through this aperture in the cover.

An advantageous embodiment of the invention is characterized in that the correct aperture in the cover where one sample at a time can be placed in the sample register is indicated by the aid of a lamp.

Another advantageous embodiment of the invention is characterized in that a computer of the apparatus carrying out the analysis points out, if necessary, the locations of the samples to be presented in desired order, by moving the sample register under the cover to the desired location, for instance by the aid of an electromotor, and the computer retains in its memory the address of the location of each presented sample subsequent to the presentation and the placing of the sample container in the sample register.

The apparatus for implementing the procedure of the invention, comprising a sample register in which the sample register sites are located at predetermined locations and in which the sample containers to be analyzed are placed, is characterized in that there is located above the sample register a cover provided with apertures so positioned that only one aperture at a time allows a sample container to be inserted through the aperture in the cover into the sample register.

An advantageous embodiment of the invention is furthermore characterized in that the sample register sites or positions are located on nested concentric circles, and that the cover over the sample register has only one aperture for each sample register circle.

BRIEF DESCRIPTION OF THE DRAWINGS

The invention is described in the following by the aid of an example, reference being made to the drawings attached, wherein.

DETAILED DESCRIPTION OF A PREFERRED EMBODIMENT

Figure 1:
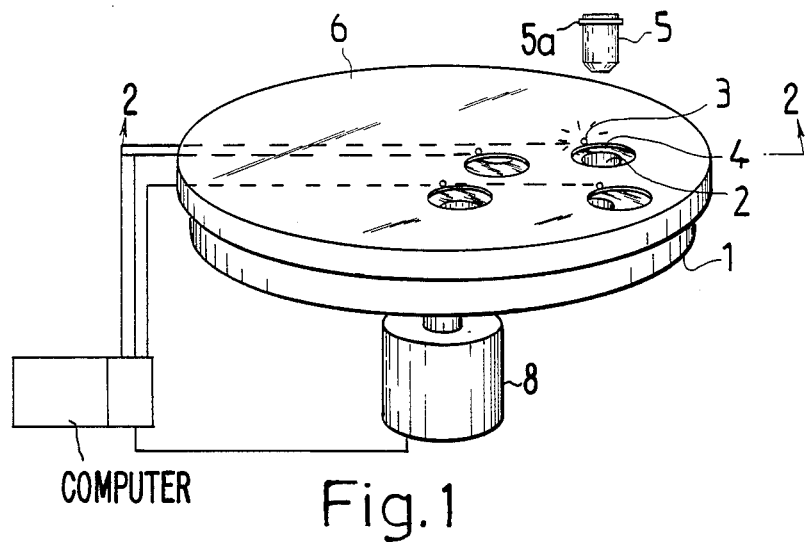
FIG. 1 presents the sample register in oblique or perspective top view, including an electro-motor and a computer schematically connected to the electromotor and sample register
Figure 2:
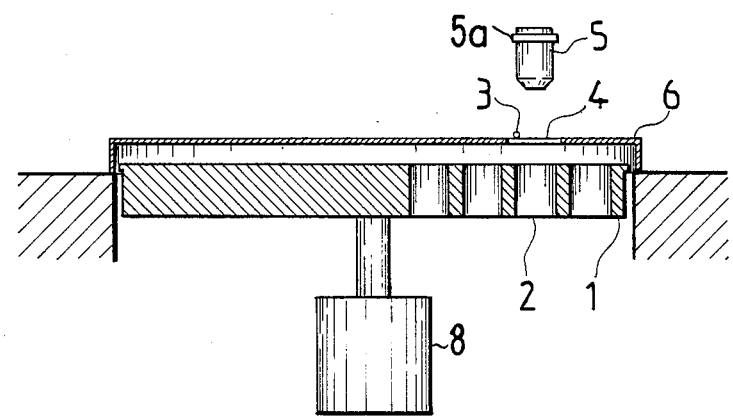
FIG. 2 presents the sample register in an elevational view and sectioned at line II—II of FIG. 1.

As shown in FIG. 1, a sample analysis apparatus includes a sample register 1 containing multiple spaced-apart openings or positions 2 located in concentric circles therein, and located below a cover 6 containing a plurality of apertures 4. The sample register 1 is rotatable relative to cover 6 by an electromotor 8 in association with a computer provided for controlling the analysis apparatus, so that only one aperture at a time is aligned with a sample register position 2. In the same register 1 of the sample analysis, apparatus, there are placed the sample containers 5 in such manner that the computer of the apparatus controls the indicator sample register 1 and the lamps 3 on its cover 6, so that only one sample container 5 at a time is insertable into an opening position 2 in the sample register 1 through an indicated aperture 4 in the cover 6. The sample container 5 is provided with a collar 5a and it goes through the aperture 4 in the cover 6, but container 5 remains suspended from its collar in the sample register 1. The address of any given sample container 5 placed into the sample registeer 1 is kept in the memory of the computer, and the computer directs or indicates the desired cup position for each sample placed, that is the sample register position 2, by rotatably moving the sample register under the cover 6 by aid of an electromotor 8 attached thereto and into alignment with the aperture 4 in the cover 6 as indicated by the lamp 3, so that the sample container 5 can be properly placed in the sample register. In this manner, the sample register 1 can be manually loaded full of patient sample container or cups 5 in those locations determined by the computer and individually indicated by the lamp 3, without any sample being wrongly placed. Thereby, the sample identification will be preserved with certainty during the analysis of the samples.

It is obvious to a person skilled in the art that the invention is not exclusively confined to the embodiment or example presented in the foregoing and that it may instead be used within the scope of the claims to be presented below in any handling of sets of sample containers where the preservation of identification is uncertain otherwise, yet of paramount importance. For instance, the sample register must not necessarily be disk-shaped with the sample registers located on nested concentric rings; in contrast, the sample register positions may be located for instance in straight rows. Equally, the apparatus can be so constructed that the sample register does not move but the cover with its apertures is movable relative to the stationary sample register.

We claim:

1. An apparatus for assuring positive identification of samples during analysis of the samples, comprising:
   a plurality of sample containers each for containing a sample material to be analyzed;
   a sample register having multiple spaced-apart discrete openings provided therein, said openings being located at pre-determined positions in a first arrangement, and into which openings the sample containers are to be placed; and
   a cover located above said sample register, said cover being provided with a plurality of discrete apertures which are so sized and located at predetermined positions in a second arrangement relative to the openings in said sample register that only a single aperture at a time can be aligned with one of said multiple openings in the sample register by movement of said sample register and said cover relative to each other, so as to allow insertion of one of said sample containers through the aperture into the aligned opening in the sample register.

2. An analyzer apparatus according to claim 1, wherein the sample register openings are located on nested concentric rings, and the cover above the sample register has only one aperture for each ring of openings provided in the sample register.

3. An analyzer apparatus according to claim 1, including an electromotor attached to the sample register and a computer operatively associated with the sample register and the electromotor, for controlling rotation of the sample register so that only one aperture at a time is aligned with the openings in the sample register.

4. An analyzer apparatus according to claim 1, wherein said sample register is rotatable relative to said cover by an electromotor attached to the sample register.

5. An analyzer apparatus for implementing a procedure for assuring the positive identification of samples to be analyzed, comprising:
   a plurality of sample containers each adapted for containing a sample material to be analyzed;
   a rotatable sample register, said sample register having a plurality of discrete openings therein, which are located at predetermined points on concentric circles, and in which openings the sample containers to be analyzed are placed, said sample register being rotatable by an electromotor attached thereto;
   a cover located above said sample register, said cover being provided with multiple discrete apertures and is so positioned relative to the rotatable sample register that only one aperture at a time is aligned with one of the sample register openings; and
   a computer operatively associated with said sample register and with the electromotor for rotating the sample register relative to the cover, whereby the sample register is so positioned relative to the cover that only one aperture at a time allows the insertion of one of said sample containers into the sample register opening location prior to performing an analysis of the sample.

6. A procedure for assuring positive identification of samples for analysis when the samples are placed in a sample register of an analyzer means for performing the analysis, said procedure comprising the steps of:
   providing a sample register having multiple spaced-apart openings located in the first predetermined arrangement therein for receiving sample containers;
   providing a cover located above said sample register, said cover having a plurality of apertures provided therein, said apertures being each sized and located in a second predetermined arrangement which is different from the first predetermined arrangement so as to allow insertion of a sample container therethrough; wherein an opening in the sample register is aligned with one said aperture provided in said cover by moving the sample register relative to the cover under control by a computer associated with an analyzer means, the correct aperture in the cover being illuminated by an indicator lamp located adjacent the aperture, then manually placing the sample container in the sample register opening through the indicated aperture in the cover, so that only one sample container at a time is placed in the sample register.

7. A procedure for assuring positive identification of samples during analysis of the samples, said procedure comprising the steps of:
   providing a sample register having a plurality of sample container receiving openings arranged therein;
   providing a cover located above said sample register, said cover having a plurality of apertures therein, said apertures being sized to allow the insertion of a sample container therethrough and being positioned on said cover so that only one aperture at a time is aligned with one of said openings;
   providing a computer adapted to control the movement of said sample register relative to said cover, and rotating the register via the computer to align only one of said apertures with one of said openings so that only a single sample container at a time can be inserted into the sample register via said aperture aligned therewith; and
   inserting a sample container through the aligned aperture and into the opening.

8. The sample identification procedure of claim 7, further comprising providing a lamp on said cover adjacent to said aperture.

9. The sample identification procedure of claim 7, wherein successive locations of sample containers being presented for sample analysis are indicated by the computer moving the sample register under the cover to a desired position by use of an electromotor attached to the sample register, so that the computer retains in its memory the position of each sample container in the register.

* * * * *